United States Patent
Kusama et al.

(10) Patent No.: US 10,670,571 B2
(45) Date of Patent: Jun. 2, 2020

(54) BIOLOGICAL GAS DETECTION DEVICE, METHOD, AND COMPUTER-READABLE STORAGE MEDIUM

(71) Applicant: Tanita Corporation, Tokyo (JP)

(72) Inventors: Ayumi Kusama, Tokyo (JP); Yasuhiro Kasahara, Tokyo (JP); Naotaka Minagawa, Tokyo (JP); Miyuki Kodama, Tokyo (JP)

(73) Assignee: Tanita Corporation, Tokyo (JP)

( * ) Notice: Subject to any disclaimer, the term of this patent is extended or adjusted under 35 U.S.C. 154(b) by 267 days.

(21) Appl. No.: 15/918,409

(22) Filed: Mar. 12, 2018

(65) Prior Publication Data

US 2018/0267004 A1    Sep. 20, 2018

(30) Foreign Application Priority Data

Mar. 15, 2017 (JP) ................................. 2017-050415

(51) Int. Cl.
*G01N 33/497*    (2006.01)
*G01N 33/00*    (2006.01)
*G01N 27/12*    (2006.01)

(52) U.S. Cl.
CPC ......... *G01N 33/007* (2013.01); *G01N 27/123* (2013.01); *G01N 27/125* (2013.01); *G01N 33/0026* (2013.01); *G01N 33/497* (2013.01)

(58) Field of Classification Search
None
See application file for complete search history.

(56) References Cited

U.S. PATENT DOCUMENTS 5,962,335 A * 10/1999 Katzman ............ A61K 51/1206
                                                        436/181
8,206,311 B2 * 6/2012 Chazan ................ G01N 21/783
                                                        600/532

(Continued)

FOREIGN PATENT DOCUMENTS

| EP | 1139099 A2 | 10/2001 |
|---|---|---|
| JP | 2016-502077 A | 1/2016 |
| WO | 2014/076493 A1 | 5/2014 |

OTHER PUBLICATIONS

Extended European Search Report issued in corresponding European Patent Application No. 181611765 dated Jul. 18, 2018.

*Primary Examiner* — Natalie Huls
*Assistant Examiner* — Jermaine L Jenkins
(74) *Attorney, Agent, or Firm* — Morgan, Lewis & Bockius LLP (57) ABSTRACT

A biological gas detection device acquires a reference output value that is an output value outputted from a semiconductor gas sensor in a reference air sample, the semiconductor gas sensor having sensitivity to an interfering gas and a target gas contained in a biological gas, acquires a target gas concentration that is a concentration of the target gas measured based on a first output value, the first output value being outputted from the semiconductor gas sensor during measurement of the biological gas, corrects the target gas concentration based on a second output value and the reference output value, the second output value being outputted from the semiconductor gas sensor in an air sample prior to measurement of the biological gas; and outputs information according to the corrected target gas concentration.

12 Claims, 7 Drawing Sheets

(56) References Cited

U.S. PATENT DOCUMENTS

| | | | |
|---|---|---|---|
| 9,671,389 B2* | 6/2017 | Van Kesteren | A61B 5/0095 |
| 10,307,080 B2* | 6/2019 | Ssenyange | A61B 5/097 |
| 2004/0018630 A1* | 1/2004 | Birks | G01N 31/005 |
| | | | 436/116 |
| 2010/0137733 A1* | 6/2010 | Wang | A61B 5/08 |
| | | | 600/532 |
| 2011/0035158 A1* | 2/2011 | Banos | A61B 5/091 |
| | | | 702/19 |
| 2013/0211207 A1 | 8/2013 | Joseph et al. | |
| 2016/0370337 A1* | 12/2016 | Blackley | G01N 33/0036 |
| 2017/0274170 A1* | 9/2017 | Haveri | G01J 5/10 |
| 2018/0074029 A1* | 3/2018 | DeVries | G01N 33/4972 |
| 2019/0017981 A1* | 1/2019 | Dutta | G01N 27/30 |

\* cited by examiner

| Lv | STRENGTH OF VENTILATION RECOMMENDATION |
|---|---|
| TH1≦Lv | 0 |
| TH2≦Lv<TH1 | 1 |
| TH3≦Lv<TH2 | 2 |
| Lv<TH3 | 3 |

BIOLOGICAL GAS DETECTION DEVICE, METHOD, AND COMPUTER-READABLE STORAGE MEDIUM

CROSS-REFERENCE TO RELATED APPLICATION

This application is based on and claims priority under 35 USC 119 from Japanese Patent Application No. 2017-050415 filed on Mar. 15, 2017, the entire contents of which is incorporated by reference herein.

BACKGROUND

Technical Field

The present invention relates to a biological gas detection device, method, and computer-readable storage medium.

Related Art

Hitherto, there have been proposals for technology to detect a biological gas component using a semiconductor gas sensor, and to acquire information related to the state of health of an organism by computing a concentration of a target gas component in the detected biological gas component.

However, a semiconductor gas sensor has sensitivity not only to the target gas component, but also has sensitivity to an interfering gas component. An interfering gas component is, for example, contained in the air, and the concentration of the interfering gas component contained in the air differs according to the peripheral environment. Thus, the responsiveness of the semiconductor gas sensor to the interfering gas component fluctuates according to the peripheral environment, making it difficult to measure the target gas alone with good precision.

Japanese Patent Application Laid-Open (JP-A) No. 2016-502077, for example, describes technology to measure peripheral air before and after a breath measurement in order to accurately find the concentration of the target gas component in a biological gas component.

However, JP-A No. 2016-502077 does not specifically describe how to accurately find the target gas component concentration in the biological gas component using the measurement results of peripheral air.

SUMMARY

An object of the present invention is to provide a biological gas detection device, method, and program capable of reducing the influence of interfering gas contained in air.

In consideration of the above circumstances, a biological gas detection device of an aspect according to the present invention includes processing circuitry configured to perform a process, the process including: acquiring a reference output value that is an output value outputted from a semiconductor gas sensor in a reference air sample, the semiconductor gas sensor having sensitivity to an interfering gas and a target gas contained in a biological gas; acquiring a target gas concentration that is a concentration of the target gas measured based on a first output value, the first output value being outputted from the semiconductor gas sensor during measurement of the biological gas; correcting the target gas concentration based on a second output value and the reference output value, the second output value being outputted from the semiconductor gas sensor in an air sample prior to measurement of the biological gas; and outputting information according to the corrected target gas concentration The aspect exhibits the advantageous effect of being able to reduce the influence of interfering gas contained in air.

DESCRIPTION OF EMBODIMENTS

Description follows regarding exemplary embodiments of the present invention.

Figure 1:
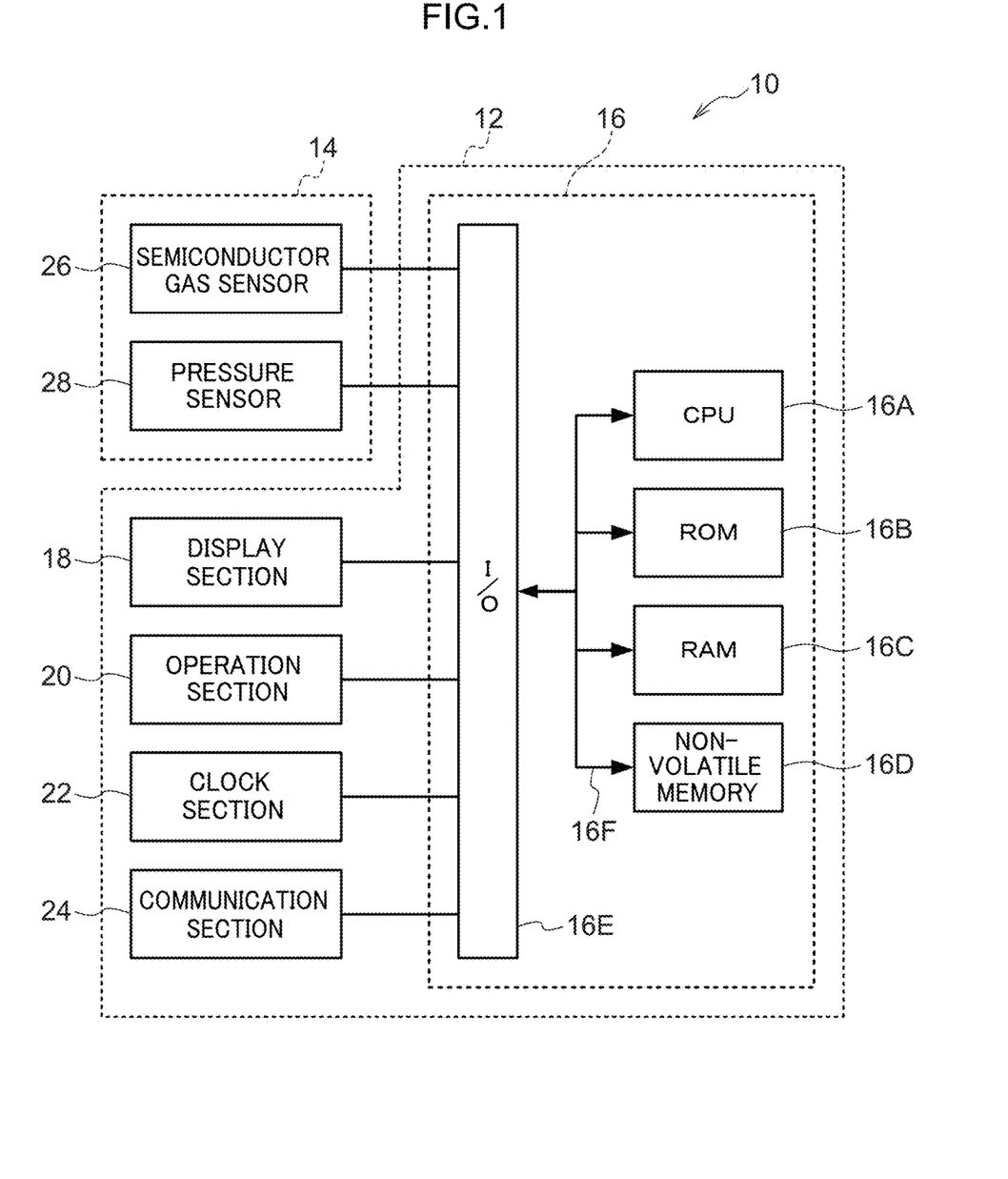
FIG. 1 is a block diagram of a biological gas detection unit.

FIG. 1 is a configuration diagram of a biological gas detection unit 10 according to an exemplary embodiment. As illustrated in FIG. 1, the biological gas detection unit 10 includes a biological gas detection device 12 and a sensor device 14. The biological gas detection device 12 includes a controller 16, a display section 18, an operation section 20, a clock section 22, and a communication section 24. The sensor device 14 includes a semiconductor gas sensor 26 and a pressure sensor 28.

The controller 16 is configured including a central processing unit (CPU) 16A, read only memory (ROM) 12B, random access memory (RAM) 16C, non-volatile memory 16D, and an input-output interface (I/O) 16E, with these being connected together through a bus 16F. In this case, a biological gas detection program to execute biological gas detection processing, described later, in the CPU 16A of the controller 16 is executed by, for example, writing the biological gas detection program to the non-volatile memory 16D and reading the biological gas detection program with the CPU 16A. Note that the biological gas detection program may be provided on a recording medium such as a CD-ROM, a memory card, or the like, or may be downloaded from a server, not illustrated in the drawings.

The display section 18, the operation section 20, the clock section 22, the communication section 24, the semiconductor gas sensor 26, and the pressure sensor 28 are connected to the I/O 16E.

The display section 18 is, for example, configured by a liquid crystal panel or the like. Various setting screens, and various results display screens, such as of detection results are, for example, displayed on the display section 18.

The operation section 20 is an operation section for a user to perform various operations.

Note that the display section 18 and the operation section 20 may be configured as a single unit using a touch panel, in a configuration in which operation can be performed by directly touching the touch panel.

The clock section 22 includes a function to acquire the current time, and a timing function to time durations.

The communication section 24 includes a function to exchange information with an external device, either by wireless communication or wired communication.

The biological gas detection device 12 may, for example, be a dedicated device, or may be a general purpose information processing device, such as a personal computer, a smartphone, a mobile phone, or a tablet terminal.

The semiconductor gas sensor 26 is a gas sensor having sensitivity to a target gas contained in a biological gas such as breath blown thereon by a user, and to an interfering gas contained in the biological gas and/or in the air. The semiconductor gas sensor 26 detects the biological gas containing the target gas and the interfering gas, and outputs a voltage value according to a mixture ratio of various gasses configuring the detected biological gas. The biological gas in the breath contains various types of gases, such as ketone bodies, ethanol, acetaldehydes, hydrogen, water vapor, methane, and various other gases of halitosis. Ketone bodies is a general term used here to indicate at least one out of acetoacetic acid, 3-hydroxy butyric acid (β-hydroxybutyric acid), or acetone.

Specifically, the semiconductor gas sensor 26 includes a metal oxide semiconductor, such as $SnO_2$, a heater, and an electrode. The metal oxide semiconductor has a resistance value that changes when a target gas and/or an interfering gas is adsorbed. Namely, the metal oxide semiconductor employed in the semiconductor gas sensor 26 has high sensitivity to trace quantities of acetone and the like, and also has sensitivity to the interfering gas.

Note that in the present exemplary embodiment, a case is described in which the target gas is acetone. Acetone is a byproduct of metabolizing fat, and the acetone concentration corresponds to the fat burn rate. Fat is not burned when there is a surplus of carbohydrate energy in the body, and so the acetone concentration is low in such cases. Fat is burned when there is insufficient carbohydrate energy in the body, and so the acetone concentration rises. This thereby enables the fat burn rate to be known from the acetone concentration.

The pressure sensor 28 detects the pressure of breath being blown thereon by a user. The pressure sensor 28 outputs the magnitude of the detected pressure as a voltage value.

Figure 2:
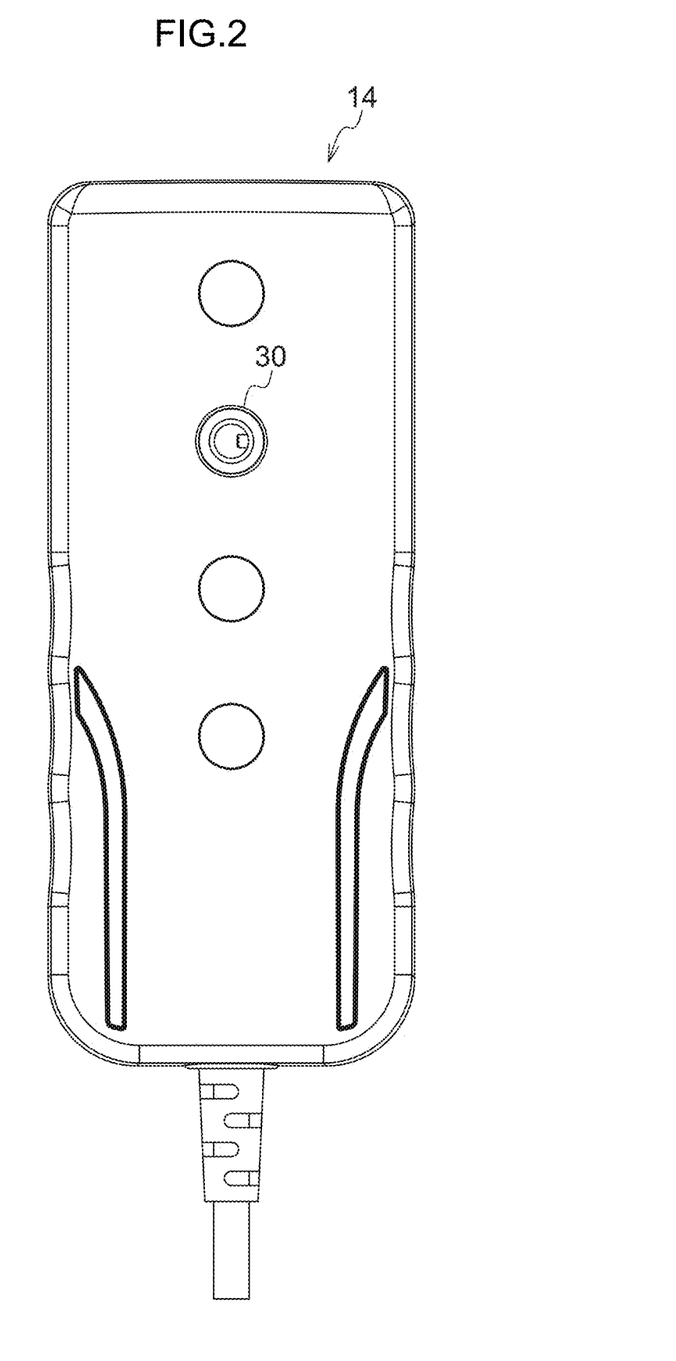
FIG. 2 is an external view of a sensor device.

FIG. 2 illustrates the external appearance of the sensor device 14. As illustrated in FIG. 2, the sensor device 14 includes a mouthpiece 30 for a user to blow breath into. When a user blows their breath into the mouthpiece 30, the target gas and interfering gas contained in the biological gas is detected by the semiconductor gas sensor 26. Note that although the sensor device 14 illustrated in FIG. 2 is connected to the biological gas detection device 12 by wire, there is no limitation thereto, and the sensor device 14 may be connected to the biological gas detection device 12 wirelessly. Moreover, the sensor device 14 and the biological gas detection device 12 may be formed as a single unit.

Figure 3:
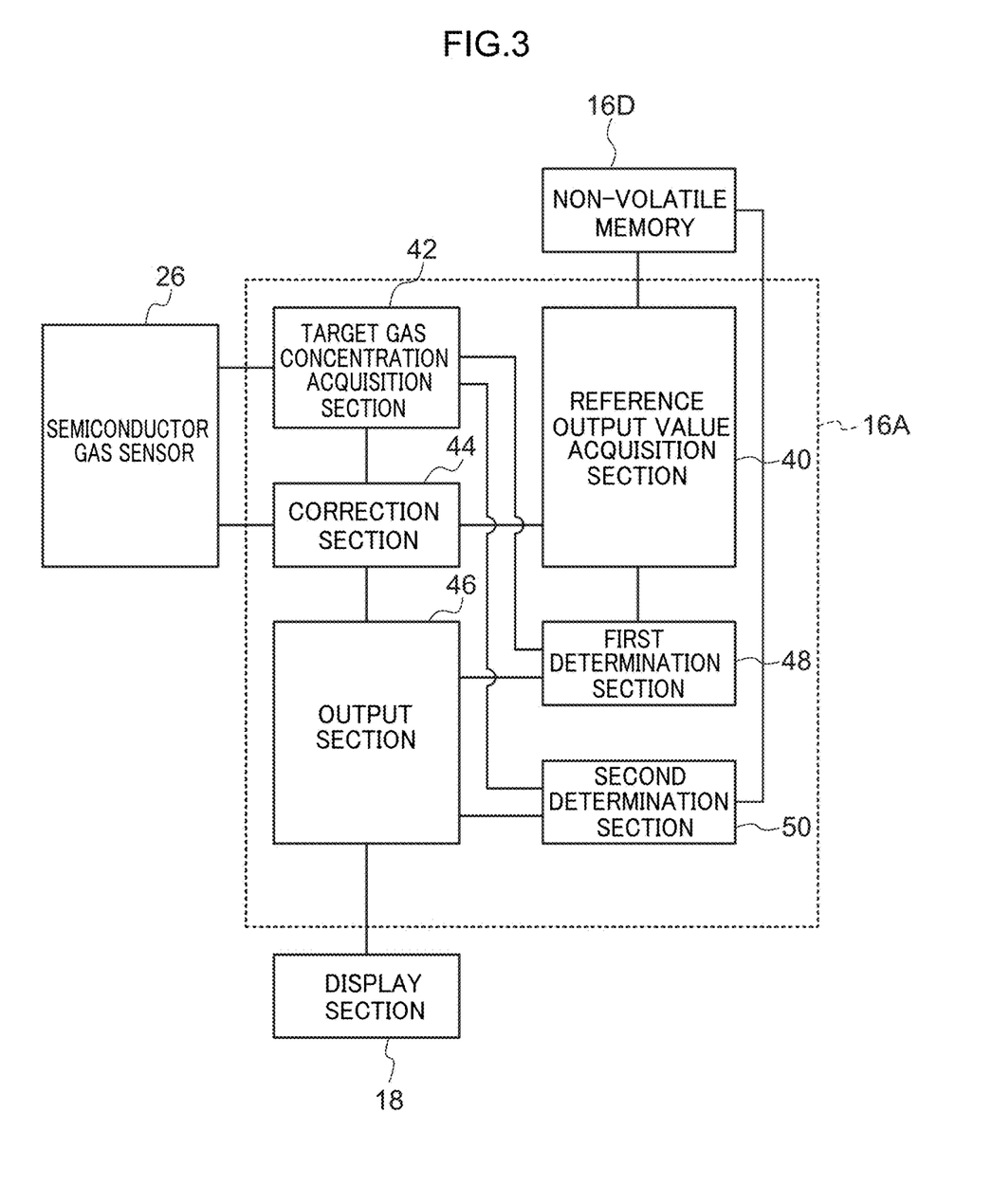
FIG. 3 is a functional block diagram of a biological gas detection device.

As illustrated functionally in FIG. 3, the CPU 16A of the controller 16 includes a reference output value acquisition section 40, a target gas concentration acquisition section 42, a correction section 44, and an output section 46. Moreover, the CPU 16A of the controller 16 may further include a first determination section 48, and a second determination section 50. The reference output value acquisition section 40 acquires a reference output value that is an output value outputted from a semiconductor gas sensor 26 in a reference air sample, where, as mentioned previously, the semiconductor gas sensor 26 has sensitivity to an interfering gas and a target gas contained in a biological gas. Note that the reference air sample is, for example, the air in an environment for manufacturing the biological gas detection unit 10, such as a factory or the like, the air of an environment for calibrating the biological gas detection unit 10, or a clean air sample. The target gas concentration acquisition section 42 acquires a target gas concentration that is a concentration of the target gas measured based on a first output value, where the first output value is outputted from the semiconductor gas sensor 26 during measurement of the biological gas. The correction section 44 corrects the target gas concentration based on a second output value and the reference output value, where the second output value is outputted from the semiconductor gas sensor 26 in an air sample prior to measurement of the biological gas. The output section 46 outputs information according to the corrected target gas concentration that was corrected by the correction section 44. The first determination section 48 determines a strength of ventilation recommendation of the measurement environment of the biological gas based on the second output value and the reference output value. The second determination section 50 determines whether or not a determination value, determined in terms of the second output value at the current measurement time and the second output value at a previous measurement time, is a threshold value or greater. Note that there is no limitation thereto, and at least one of the reference output value acquisition section 40, the target gas concentration acquisition section 42, the correction section 44, the output section 46, the first determination section 48, and the second determination section 50 may be configured by separate hardware, such as an application specific integrated circuit (ASIC).

Figure 4:
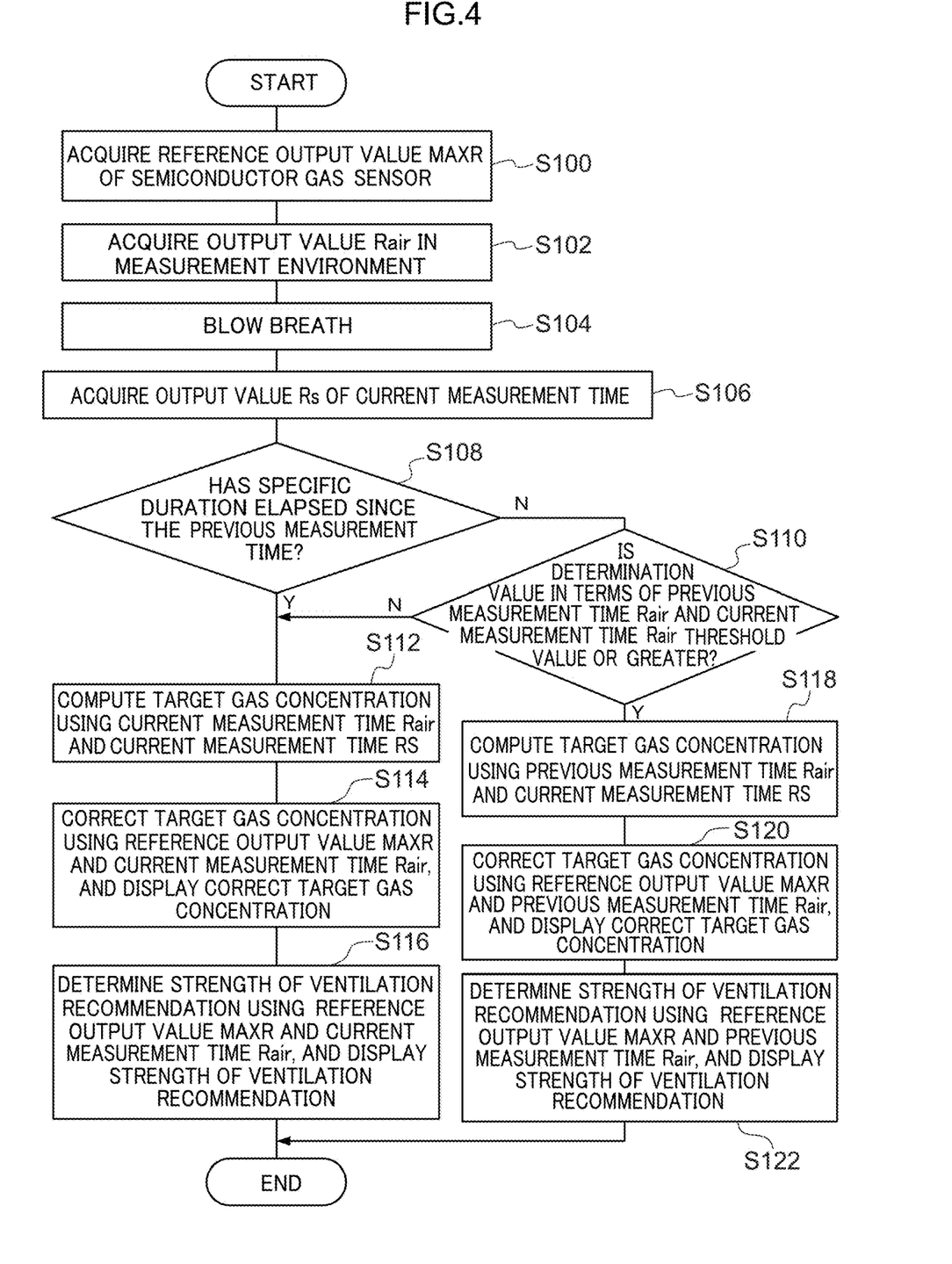
FIG. 4 is a flowchart of processing by a biological gas detection program.

Description now follows regarding processing by a biological gas detection program executed in the CPU 16A of the controller 16 as operation of the present exemplary embodiment, with reference to the flowchart illustrated in FIG. 4. Note that the processing illustrated in FIG. 4 is executed in cases in which execution of the biological gas detection program has been instructed by a user operating the operation section 20 of the biological gas detection device 12. Note that the processing illustrated in FIG. 4 may be executed on detecting blowing by the user.

At step S100, the reference output value acquisition section 40 reads and acquires a reference output value MAXR of the semiconductor gas sensor 26 from the non-volatile memory 16D. The reference output value MAXR of the semiconductor gas sensor 26 is, for example, an output value of the semiconductor gas sensor 26 acquired in a reference air sample, and is stored in advance in the non-volatile memory 16D.

At step S102, the target gas concentration acquisition section 42 acquires an output value Rair of the semiconductor gas sensor 26 (the second output value) in an air sample prior to measurement of the biological gas, and stores the output value Rair in the non-volatile memory 16D. Namely, the output value Rair of the semiconductor gas sensor 26 is acquired in the usage environment of the biological gas detection unit 10 by a user, prior to the user blowing breath on the sensor device 14. The output value of the semiconductor gas sensor 26 in the air of the measurement environment is thereby obtained.

At step S104, the target gas concentration acquisition section 42 displays on the display section 18 a message prompting a user to breath so as to blow onto the mouthpiece 30, so as have the user blow onto the mouthpiece 30.

At step S106, the target gas concentration acquisition section 42 acquires an output value Rs of the semiconductor gas sensor 26 (the first output value). Note that there are many gas components of air contained in breath immediately after starting to blow. Thus, preferably the end of a breath after completely expelling the gas components of the air is utilized when computing the concentration of target gas related to the fat burn rate. Namely, the output value of the semiconductor gas sensor 26 at a timing to obtain the end of a breath is preferably employed as the first output value. Thus, timing by the clock section 22 is started at the point in time when the blowing of a breath is detected, and the output value of the semiconductor gas sensor 26 at a point in time when a predetermined duration (for example, 4 seconds) has elapsed is preferably employed as the first output value.

Note that determination as to whether or not a breath has been blown may, for example, be performed by acquiring an output value of the pressure sensor 28 and determining whether or not the output value acquired from the pressure sensor 28 is a predetermined threshold value or greater.

At step S108, the target gas concentration acquisition section 42 determines whether or not a change amount per unit time of the output value of the semiconductor gas sensor 26 (namely, the second output value) is stable by determining whether or not a specific duration has elapsed since the previous measurement time. This is because, if the output value of the semiconductor gas sensor 26 in the air was to be acquired successively without providing sufficient waiting time from the previous measurement time, then there would be an influence from the biological gas from the previous measurement time remaining in the vicinity of the semiconductor gas sensor 26, with the output value Rair being acquired in a state containing this biological gas.

Note that the measurement time is the point in time when the output value Rs of the semiconductor gas sensor 26 (the first output value) is acquired at step S106. Moreover, the previous measurement time is, from out of past times that the processing of FIG. 4 was executed, a time that is both a time when the output value of the semiconductor gas sensor 26 (the second output value) has been obtained with a stable change amount per unit time at step S102 and that is the most recent time.

Moreover, the specific duration is set to a duration equivalent to when a change amount per unit time of the output value of the semiconductor gas sensor 26 has stabilized, namely, to a duration when determination can be made that the biological gas from the previous measurement time does not remain in the vicinity of the semiconductor gas sensor 26. Note that whether or not the change amount per unit time of the output value of the semiconductor gas sensor 26 is stable may be determined by computing the change amount per unit time of the output value of the semiconductor gas sensor 26 and determining whether or not the computed change amount is a predetermined threshold value or lower.

Processing transitions to step S112 when determination at step S108 is affirmative determination, namely, when it has been determined that the change amount per unit time of the output value of the semiconductor gas sensor 26 is stable. However, processing transitions to step S110 when determination at step S108 is negative determination, namely, when it has been determined that the change amount per unit time of the output value of the semiconductor gas sensor 26 is not stable.

At step S112, based on the output value Rair acquired at the current measurement time at step S102 and on the output value Rs acquired at the current measurement time at step S106, the target gas concentration acquisition section 42 computes a target gas concentration D1 in the biological gas according to the following equation.

$$D1 = f1(Rair, Rs) \tag{1}$$

In Equation (1) above, the function f1 is an operational expression including output value Rair and the output value Rs as variables. The operational expression is not limited to being a linear equation, and may be a polynomial equation of quadratic or higher order. The operational expression may also include operators such as reciprocals, exponentials, and logarithms. Note that coefficients in the operational expression are, for example, set based on results of executing calibration of the output values when shipping the biological gas detection unit 10 from a factory, and are coefficients determined using the reference output value MAXR.

At step S114, based on the reference output value MAXR acquired at step S100 and on the output value Rair acquired at the current measurement time at step S102, the correction section 44 corrects the target gas concentration D1 computed at step S112 using the following equation, and acquires a corrected target gas concentration D2.

$$D2 = f2(D1, Rair) \tag{2}$$

Note that in Equation (2) above, the function f2 is an operational expression including target gas concentration D1 and output value Rair as variables. The operational expression is not limited to being a linear equation, and may be a polynomial equation of quadratic or higher order. The operational expression may also include operators such as reciprocals, exponentials, and logarithms. Note that coefficients in the operational expression are, for example, coefficients determined using the reference output value MAXR.

The corrected target gas concentration D2 computed according to above Equation (2) is then output to and displayed on the display section 18.

At step S116, based on the reference output value MAXR acquired at step S100 and on the output value Rair acquired at the current measurement time at step S102, the first determination section 48 determines the strength of ventilation recommendation, and the output section 46 outputs the strength of ventilation recommendation determined by the first determination section 48 to the display section 18, thereby displaying the strength of ventilation recommendation on the display section 18. The strength of ventilation recommendation here is an index expressing an amount of interfering gas in the air.

Specifically, for example, a determination value Lv to determine the strength of ventilation recommendation is computed according to the following equation.

$$Lv = f(MAXR, Rair) \tag{3}$$

The f(MAXR, Rair) here is an operational expression to compute the determination value Lv using the reference output value MAXR and the output value Rair acquired at the current measurement time at step S102 as parameters.

Figure 5:
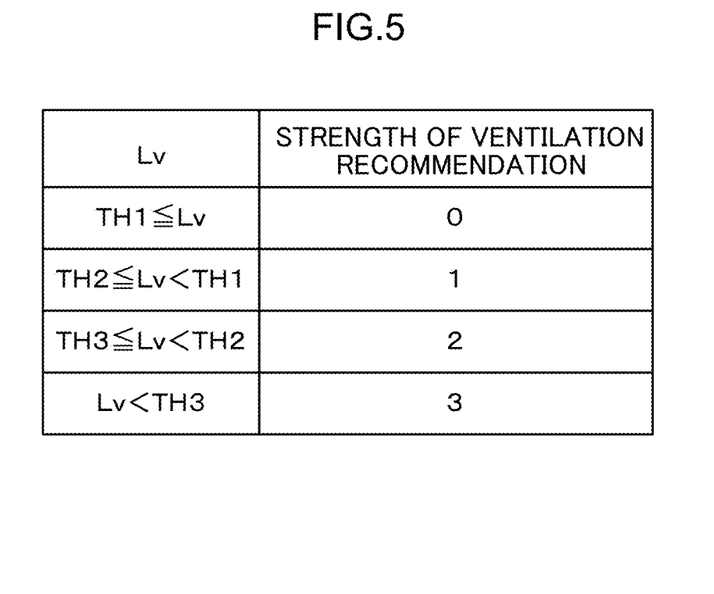
FIG. 5 is a diagram illustrating relationships between a strength of ventilation recommendation and a ventilation requirement determination value.

Then, for example as illustrated in FIG. 5, the strength of ventilation recommendation corresponding to the determination value Lv is found based on the correspondence relationship between the determination value Lv and the strength of ventilation recommendation. In the example of FIG. 5, the strength of ventilation recommendation is "0" when the determination value Lv is a threshold value TH1 or greater. Moreover, the strength of ventilation recommendation is "1" when the determination value Lv is a threshold value TH2 or greater but less than the threshold value TH1. Moreover, the strength of ventilation recommendation is "2"

when the determination value Lv is a threshold value TH3 or greater but less than the threshold value TH2. Moreover, the strength of ventilation recommendation is "3" when the determination value Lv is less than the threshold value TH3. Namely, as the value of the determination value Lv increases (as output value Rair approaches reference output value MAXR), the strength of ventilation recommendation decreases (the need for ventilation is less), and as the value of the determination value Lv decreases (as output value Rair moves away from the reference output value MAXR), the strength of ventilation recommendation increases (the need for ventilation is greater).

At step S110, the second determination section 50 reads, from the non-volatile memory 16D, an output value Rair 0 acquired at step S102 at the previous measurement time, and determines whether or not a determination value A, determined in terms of the output value Rair from the previous measurement time that has been read and the output value Rair acquired at step S102 at the current measurement time, is a predetermined threshold value or greater. By performing the determination of step S110 in this manner only after the determination at step S108, the processing load is reduced compared to cases in which the determination of step S110 is always performed.

The determination value A may, for example, be computed according to the following equation, where the output value at the previous measurement time is Rair A and the output value at the current measurement time is Rair B.

$$A = f(\text{Rair } A, \text{Rair } B) \quad (5)$$

Wherein, f(Rair A, Rair B) is an operational expression to compute determination value A using the previous measurement time output value Rair A and the current measurement time output value Rair B as parameters. This operational expression is an operational expression in which the greater the difference between the previous measurement time output value Rair A and the current measurement time output value Rair B, the larger the value of determination value A.

Moreover, in cases in which the determination value A is the predetermined threshold value or greater, namely, in cases in which it is not appropriate to compute the target gas concentration D using the current measurement time output value Rair B, processing transitions to step S118. However, in cases in which the determination value A is less than the predetermined threshold value, namely, in cases in which the target gas concentration D may be computed using the current measurement time output value Rair B, processing transitions to step S112.

At step S118, based on the output value Rair acquired at step S102 at the previous measurement time and on the output value Rs acquired at step S106 at the current measurement time, the target gas concentration acquisition section 42 computes the target gas concentration D1 included in the biological gas according to the above Equation (1).

Namely, affirmative determination at step S110 is taken as indicating that measurement was performed successively without providing sufficient waiting time, and the target gas concentration D1 is computed using the output value Rair at measurement the previous measurement time instead of using the output value Rair at the current measurement time.

Figure 6:
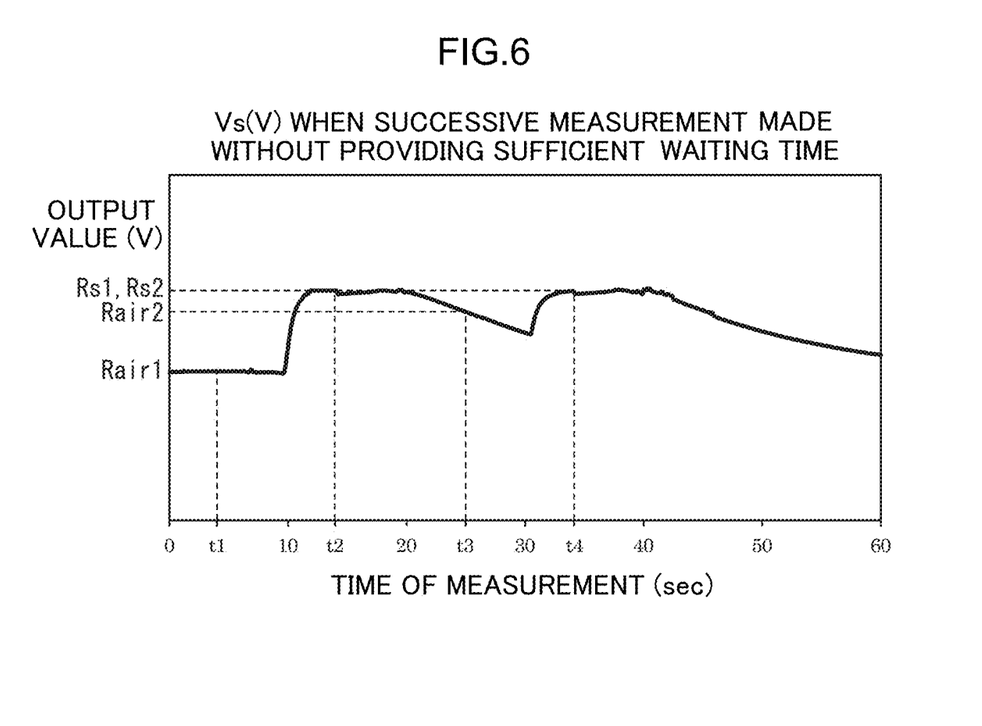
FIG. 6 is a line graph illustrating an example of an example of changes in output value of a semiconductor gas sensor.

FIG. 6 illustrates an example of changes to output value (V) of the semiconductor gas sensor 26 in cases in which subsequent measurements are made without providing sufficient waiting time. As illustrated in FIG. 6, in cases in which power to the biological gas detection unit 10 is switched on and a first time output value Rair 1 of the semiconductor gas sensor 26 is acquired at a point in time t1, the output value Rair 1 is an output value in an air sample acquired at a point in time when determination can be made that there is no biological gas in the vicinity of the semiconductor gas sensor 26. The output value of the semiconductor gas sensor 26 then rises due to a user blowing a breath thereon, and a first output value Rs1 is acquired at a point in time t2. Subsequently, when breath is no longer being blown by the user, the output value of the semiconductor gas sensor 26 then gradually decreases. Then if a second time output value Rair 2 is acquired at a point in time t3 prior to the output value of the semiconductor gas sensor 26 falling to Rair 1, due to being influenced by the biological gas at the previous measurement time remaining in the vicinity of the semiconductor gas sensor 26, the output value Rair 2 is an inaccurate value as the second output value, which is the output value of the semiconductor gas sensor 26 in the air. Thus, as illustrated in FIG. 6, even supposing that the second time output value Rs 2 acquired at a point in time t4 is the same value as the first time output value Rs 1, due to the values of the output value Rair 1 and the output value Rair 2 in the air being greatly different from each other, the target gas can no longer be computed with good precision.

Therefore, instead of using the output value Rair 2 acquired at the point in time t3, the target gas concentration D1 is computed based on the output value Rair 1 acquired at the point in time t1 and the second time output value Rs 2 acquired at the point in time t4.

At step S120, based on the reference output value MAXR acquired at step S100 and the output value Rair at the previous measurement time acquired at step S102, the correction section 44 corrects the target gas concentration D1 computed at step S118 according to above Equation (2).

Then, the corrected target gas concentration D2 computed according to above Equation (2) is output to and displayed on the display section 18.

At step S122, based on the reference output value MAXR acquired at step S100 and the output value Rair acquired at step S102 at the previous measurement time, the first determination section 48 computes the determination value Lv according to above Equation (3). Then, similarly to at step S116, the strength of ventilation recommendation is found that corresponds to the determination value Lv. Then the output section 46 outputs the strength of ventilation recommendation found by the first determination section 48 to the display section 18 and displays the strength of ventilation recommendation on the display section 18. In this manner, a strength of ventilation recommendation can be determined in which the influence of the biological gas from the previous measurement time remaining in the vicinity of the semiconductor gas sensor 26 is reduced, by determining the strength of ventilation recommendation using the output value Rair A for the previous measurement time instead of the output value Rair B for the current measurement time.

Note that although, hitherto, sufficient waiting time needed to be provided when measuring, in the present exemplary embodiment, by using the output value Rair of the previous measurement time, the target gas concentration and the strength of ventilation recommendation are computed and displayed at steps S120, S122 even in cases in which subsequent measurements are made without providing sufficient waiting time. Namely, the displayed target gas concentration and strength of ventilation recommendation could be said to be less accurate in comparison to the target gas concentration and strength of ventilation recommendation computed at steps S114, S116. Thus, after the processing of step S122, for example, a message may be displayed on the display section 18 stating that "This is a measurement result in quick mode". The user can thereby be readily made aware that the target gas concentration and the strength of ventilation recommendation displayed are less accurate computations thereof.

In this manner, in the present exemplary embodiment, the target gas concentration is corrected based on the reference output value MAXR of the semiconductor gas sensor 26 acquired in a clean air sample at factory shipment and on the output value Rair when the breath was blown thereon previously in the measurement environment, enabling the target gas to be detected with good precision even under the influence of interfering gas.

Moreover, even in cases in which subsequent measurements are performed without waiting a sufficient waiting time since the previous measurement time, the target gas concentration D is computed using the previous measurement time output value Rair and corrected, enabling the target gas concentration D to be computed with good precision, and while also enabling the waiting time for a subsequent measurement to be shortened.

Moreover, the strength of ventilation recommendation found based on the reference output value MAXR and the current measurement time or previous measurement time output value Rair is displayed, enabling a user to easily ascertain whether or not the current environment is an environment suitable for measurement. In this manner, due to acquiring the target gas concentration using the previous measurement time output value Rair A instead of the current measurement time output value Rair B, a target gas concentration can be acquired for which the influence due to biological gas from the previous measurement time remaining in the vicinity of the semiconductor gas sensor 26 is reduced.

TEST EXAMPLES

A description follows regarding test examples of the present invention.

Figure 7:
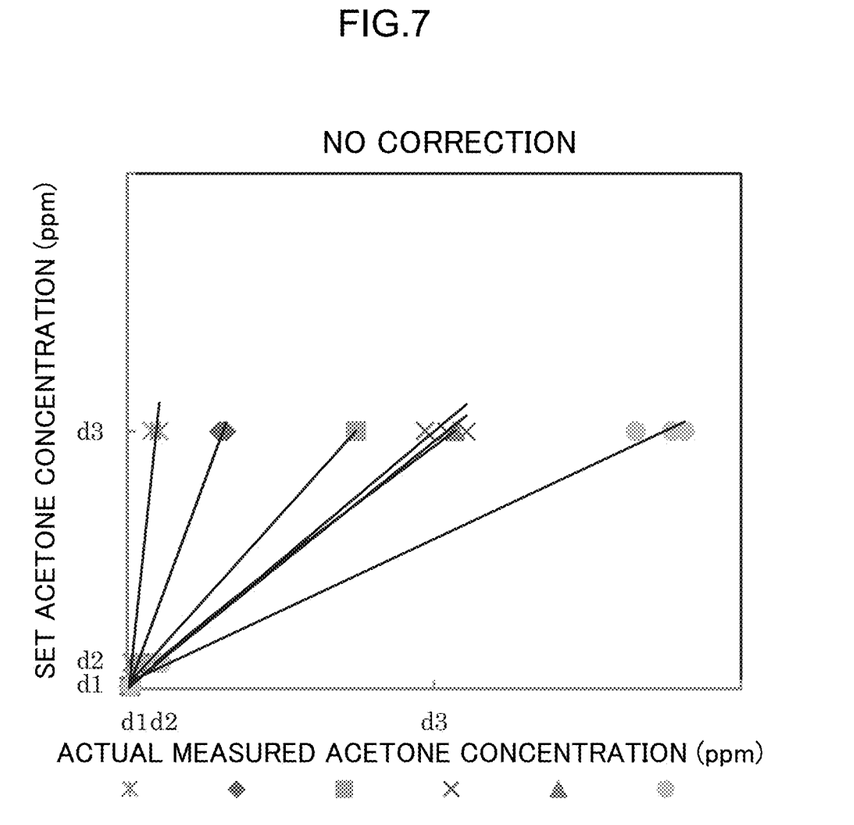
FIG. 7 is a diagram illustrating measurement results when acetone concentrations measured under different environmental conditions are not corrected.

FIG. 7 illustrates results for cases in which acetone concentration was measured using acetone-containing-gases containing different amounts of acetone in environmental conditions of each of six different patterns (asterisk, black diamond, black square, black cross, black triangle, black circle) of air state, without the acetone concentrations being corrected. Note that the acetone-containing-gases employed were three types containing acetone concentrations (set acetone concentrations) of d1, d2, d3. Note that d1 has the lowest concentration from out of the three types of set acetone concentration d1 to d3, and d3 has the highest concentration thereof. Moreover, in the measurements, the acetone concentration was measured for the acetone-containing-gas of each of the three types of set acetone concentration in each of the six patterns of environmental condition. Note that these measurements were performed repeatedly multiple times. The solid lines in the graph illustrated in FIG. 7 are straight line passing through approximations to the repeatedly performed measurement results. The vertical axis indicates the set acetone concentration, and the horizontal axis indicates the measurement value of the acetone concentration without correction (the actual measured acetone concentration).

Figure 8:
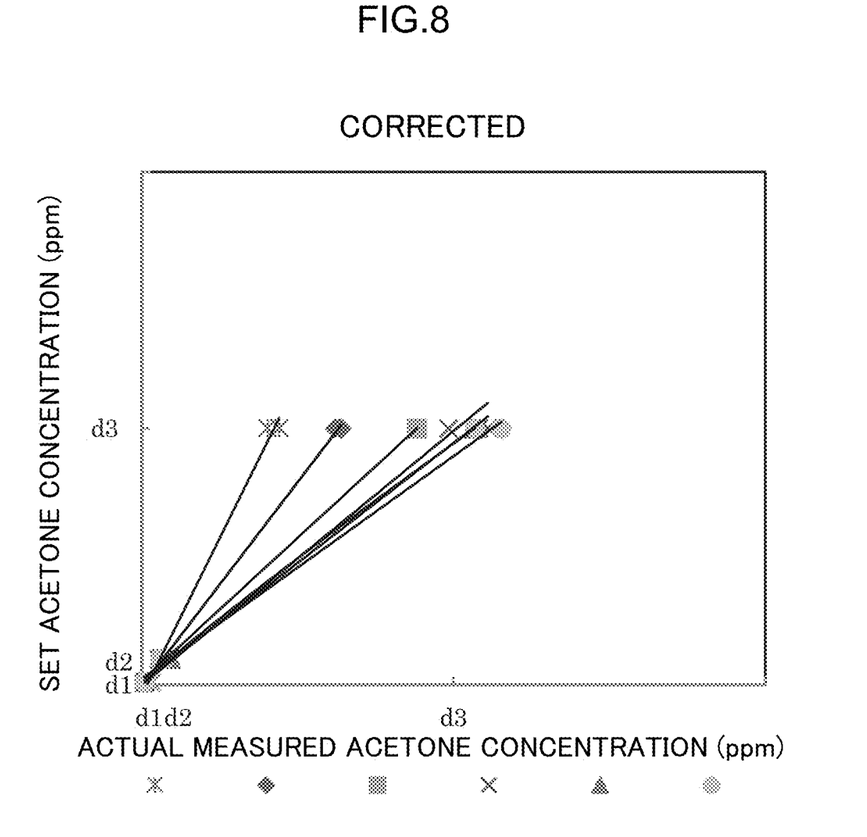
FIG. 8 is diagram illustrating measurement results when acetone concentrations measured under different environmental conditions have been corrected.

Moreover, similarly to in FIG. 7, FIG. 8 illustrates results for cases in which acetone concentrations are measured for acetone-containing-gases of each of the three types of set acetone concentration in each of the six patterns of environmental condition, and the acetone concentrations corrected as per the present exemplary embodiment. The vertical axis indicates the set acetone concentration, and the horizontal axis indicates the actual measured acetone concentrations with correction.

Although there is a large variation in measured acetone concentration in cases in which the acetone concentration was uncorrected, as is apparent from the 10 ppm case as shown by the actual measured acetone concentration with a set acetone concentration of d3 in FIG. 7, it can be seen that the variation is smaller in cases in which the acetone concentration had been corrected, as illustrated in FIG. 8. Namely, it can be seen that the acetone concentration can be measured with good precision by correcting the acetone concentration as per the present exemplary embodiment, even when environmental conditions differ.

Note that although explanation has been given in the present exemplary embodiment regarding a case in which the target gas was acetone, the concentration of acetaldehyde contained in a biological gas is low in a healthy subject, for example, but the acetaldehyde concentration is high for a subject with a bad liver. Thus, the concentration of acetaldehyde as the target gas may be found. This enables the state of the liver to be ascertained with good precision. Moreover, the biological gas serving as the object of detection is not limited to a biological gas contained in the breath, and, for example, may be a biological gas arising from the skin.

What is claimed is:

1. A biological gas detection device comprising:
   processing circuitry configured to perform a process, the process including:
   acquiring a reference output value that is an output value outputted from a semiconductor gas sensor in a reference air sample, the semiconductor gas sensor having sensitivity to an interfering gas and a target gas contained in a biological gas;
   acquiring a target gas concentration that is a concentration of the target gas measured based on a first output value, the first output value being outputted from the semiconductor gas sensor during measurement of the biological gas;
   correcting the target gas concentration based on a second output value and the reference output value, the second output value being outputted from the semiconductor gas sensor in an air sample prior to measurement of the biological gas; and
   outputting information according to the corrected target gas concentration.

2. The biological gas detection device of claim 1, wherein the process further comprises:
   determining a strength of ventilation recommendation of a measurement environment of the biological gas based on the second output value and the reference output value, and
   outputting information according to the determination result.

3. The biological gas detection device of claim 2, wherein the process further comprises:
   determining whether or not a determination value defined in terms of the second output value at a current measurement time and the second output value at a previous measurement time is a threshold value or greater,
   correcting the target gas concentration using the second output value at the current measurement time if the determination value is less than the threshold value, and
   correcting the target gas concentration using the second output value at the previous measurement time if the determination value is the threshold value or greater.

4. The biological gas detection device of claim 3, wherein the process further comprises:
  if the determination value is less than the threshold value, acquiring the target gas concentration based on the first output value at the current measurement time and the second output value at the current measurement time; and
  if the determination value is the threshold value or greater, acquiring the target gas concentration based on the first output value at the current measurement time and the second output value at the previous measurement time.

5. The biological gas detection device of claim 4, wherein the process further comprises:
  determining whether or not the determination value is the threshold value or greater in cases in which output values of the semiconductor gas sensor are not stable since measurement at the previous measurement time.

6. The biological gas detection device of claim 3 wherein the process further comprises:
  determining whether or not the determination value is the threshold value or greater in cases in which output values of the semiconductor gas sensor are not stable since measurement at the previous measurement time.

7. The biological gas detection device of claim 1, wherein the process further comprises:
  determining whether or not a determination value defined in terms of the second output value at a current measurement time and the second output value at a previous measurement time is a threshold value or greater,
  correcting the target gas concentration using the second output value at the current measurement time if the determination value is less than the threshold value, and
  correcting the target gas concentration using the second output value at the previous measurement time if the determination value is the threshold value or greater.

8. The biological gas detection device of claim 7, wherein the process further comprises:
  if the determination value is less than the threshold value, acquiring the target gas concentration based on the first output value at the current measurement time and the second output value at the current measurement time; and
  if the determination value is the threshold value or greater, acquiring the target gas concentration based on the first output value at the current measurement time and the second output value at the previous measurement time.

9. The biological gas detection device of claim 8, wherein the process further comprises:
  determining whether or not the determination value is the threshold value or greater in cases in which output values of the semiconductor gas sensor are not stable since measurement at the previous measurement time.

10. The biological gas detection device of claim 7, wherein the process further comprises:
  determining whether or not the determination value is the threshold value or greater in cases in which output values of the semiconductor gas sensor are not stable since measurement at the previous measurement time.

11. A biological gas detection method comprising:
  acquiring a reference output value that is an output value outputted from a semiconductor gas sensor in a reference air sample, the semiconductor gas sensor having sensitivity to an interfering gas and a target gas contained in a biological gas;
  acquiring a target gas concentration that is a concentration of the target gas measured based on a first output value, the first output value being outputted from the semiconductor gas sensor during measurement of the biological gas;
  correcting the target gas concentration based on a second output value and the reference output value, the second output value being outputted from the semiconductor gas sensor in an air sample prior to measurement of the biological gas; and
  outputting information according to the corrected target gas concentration.

12. A non-transitory computer-readable storage medium storing a biological gas detection program executable to cause processing circuitry to perform processing, the processing comprising:
  acquiring a reference output value that is an output value outputted from a semiconductor gas sensor in a reference air sample, the semiconductor gas sensor having sensitivity to an interfering gas and a target gas contained in a biological gas;
  acquiring a target gas concentration that is a concentration of the target gas measured based on a first output value, the first output value being outputted from the semiconductor gas sensor during measurement of the biological gas;
  correcting the target gas concentration based on a second output value and the reference output value, the second output value being outputted from the semiconductor gas sensor in an air sample prior to measurement of the biological gas; and
  outputting information according to the corrected target gas concentration.

* * * * *